(12) United States Patent
Santopietro et al.

(10) Patent No.: US 11,904,028 B2
(45) Date of Patent: Feb. 20, 2024

(54) SECURITY MECHANISMS FOR RADIOPHARMACEUTICAL ELUTION SYSTEM AND ELUTION PROCESS

(71) Applicant: Jubilant Draximage Inc., Kirkland (CA)

(72) Inventors: Riccardo Santopietro, Pierrefonds (CA); Robert William Riddoch, Pierrefonds (CA); Paul Donnelly, L'Ile Bizard (CA); Etienne Lefort, Kirkland (CA); Cristian-Leonardo Juverdianu, Dorval (CA)

(73) Assignee: Jubilant Draximage Inc., Kirkland (CA)

( * ) Notice: Subject to any disclaimer, the term of this patent is extended or adjusted under 35 U.S.C. 154(b) by 330 days.

(21) Appl. No.: 16/832,412

(22) Filed: Mar. 27, 2020

(65) Prior Publication Data

US 2020/0306393 A1   Oct. 1, 2020

Related U.S. Application Data

(60) Provisional application No. 62/826,730, filed on Mar. 29, 2019.

(51) Int. Cl.
*A61K 51/12* (2006.01)
*G21F 5/015* (2006.01)
*G21G 4/08* (2006.01)

(52) U.S. Cl.
CPC .......... *A61K 51/1217* (2013.01); *G21F 5/015* (2013.01); *G21G 4/08* (2013.01)

(58) Field of Classification Search
None
See application file for complete search history.

(56) References Cited

U.S. PATENT DOCUMENTS 4,683,123 A    7/1987  Knapp et al.
2008/0277594 A1*  11/2008  Wagner .................. G21F 5/018
                                                              250/432 PD (Continued)

FOREIGN PATENT DOCUMENTS

WO    2014/036627 A1    3/2014
WO    2018/057634 A1    3/2018

OTHER PUBLICATIONS

Yu et al., J. Pharm. Biomed. Anal., 2002, 29(5), 969.

*Primary Examiner* — Andrew Smyth
(74) *Attorney, Agent, or Firm* — BakerHostetler

(57) ABSTRACT

A radioisotope elution system is provided, that has at least a component comprised in a cabinet and accessible via a door equipped with an authentication system to ensure safety. The system may also have a user interface equipped with an authentication system. It is also provided a radioisotope elution system that has a dose calibrator equipped with a lifting mechanism for lifting and/or lowering the vial to be tested in the dose calibrator. Advantageously, the lifting mechanism may be controlled for preventing the vial from being lifted during a quality control test on a sample of eluate in the vial. This feature prevents a user from tampering and/or interfering with the vial while a quality control testing is in progress. In another feature, there is provided a radioisotope elution system with a scanning system for entering information about the radioisotope generator and/or the patient in the system. Systems ensuring that the eluant reservoir contains a saline solution are proposed.

14 Claims, 2 Drawing Sheets

(56) References Cited

U.S. PATENT DOCUMENTS

2014/0374614 A1* 12/2014 Hidem .................. A61M 5/158
    250/393
2015/0238918 A1* 8/2015 Khachaturian ...... B01J 19/0093
    422/119
2018/0296751 A1* 10/2018 Lefort .................... G16H 20/40

* cited by examiner

SECURITY MECHANISMS FOR RADIOPHARMACEUTICAL ELUTION SYSTEM AND ELUTION PROCESS

CROSS-REFERENCE TO RELATED APPLICATIONS

The present application claims the benefit of priority to U.S. Provisional Application Ser. No. 62/826,730, filed Mar. 29, 2019, the entire contents of which are incorporated herein by reference.

TECHNICAL FIELD

The present invention relates in general to nuclear medicine and, in particular, to radiopharmaceutical elution systems for the generation of a radiopharmaceutical composition for treating and/or diagnosing a disease or a condition.

BACKGROUND

Radioisotopes play a pivotal role in the diagnosis and treatment of various diseases. For example, $^{131}$I in treatment of hyperthyroidism and thyroid cancer, $^{177}$Lu in the treatment of neuroendocrine and prostate cancer, $^{68}$Ga and $^{18}$F in oncology imaging, $^{11}$C in neurology imaging and $^{99m}$Tc and $^{82}$Rb as tracers in myocardial perfusion imaging. The radioisotopes for pharmaceutical use are produced either by bombardment in a cyclotron, linear accelerators or nuclear reactors in specially approved remote sites or in-situ by employing radioisotope generators at the site of use.

Radiopharmaceutical devices are complex and there is a high risk of radiation hazard and accidental exposure to user. Unauthorized access to components of generator system and elution system should be controlled or monitored by allowing only the authorized personnel to handle such equipment. Accordingly, there is a need to restrict/control/monitor the access to such equipment by authorized person only.

Rubidium ($^{82}$Rb) is used as a positron emission tomography (PET) tracer for non-invasive measurement of perfusion. Rubidium-82 is produced in situ by radioactive decay of strontium-82. Rubidium elution systems utilize doses of rubidium-82 generated by elution within a radioisotope generator, and infuse the radioactive solution into a patient. The infused dose of radiopharmaceutical is absorbed by cells of a target organ of the patient and emit radiation which is detected by a PET scanner in order to generate an image of the organ.

There is a need for improving security mechanisms thereof and preventing human errors.

SUMMARY

The present invention aims to provide a cabinet structure for radiopharmaceutical elution system with a user authentication system on each door for preventing unauthorized access to the generator and to the user interface.

The present invention concerns any of the following items:

1. A radioisotope elution system comprising a radioisotope generator containing a parent radioisotope that decays into a daughter radioisotope, a patient line for infusing a patient with a daughter radioisotope eluate generated by the generator, a pump for pumping an eluant from an eluant reservoir into the generator, a controller, and a user interface, wherein the system has at least mechanism for identifying whether the eluant is a saline solution or not, said mechanism comprises at least one of the following:
    a. configurations of the controller for providing instructions to a user to enter an information related to an eluant reservoir when said eluant reservoir is installed on the system, said information comprising at least one of a bar code number, a national drug code (NDC), a drug identification number (DIN), or the nature of the eluant; and
    b. a liquid parameter detector, wherein the liquid parameter detector that is adapted to detect in the eluant or the eluate at least one of the following parameters:
        i. pH,
        ii. refractive index,
        iii. presence divalent ions or trivalent ions,
        iv. quantity of divalent ions or trivalent ions,
        v. conductivity,
        vi. piezoelectricity,
        vii. light absorbance (detected by atomic absorption spectroscopy, based on absorption of light of free metallic ions),
        viii. photoelectricity (detected by flame photometry), atomic emission (detected by atomic emission spectroscopy (AES)),
        ix. optical emission (detected by inductively coupled plasma atomic emission spectroscopy (ICP-AES) also referred to as inductively coupled plasma optical emission spectrometry (ICP-OES)),
        x. atomic mass (detected by inductively coupled plasma mass spectrometry (ICP-MS)),
        xi. EDTA complexing ability,
        xii. fluorescence (detected by X-ray fluorescence (XRF))
        xiii. element content (detected by a particle-Induced X-Ray Emission (PIXE)).
2. The radioisotope elution system of item 1, wherein said information is not a bar code.
3. The radioisotope elution system of item 1, wherein said information comprises at least one of a bar code number, or a national drug code (NDC).
4. The radioisotope elution system of any one of items 1 to 3, wherein the system further comprises a printer, and wherein the controller controls the printer and, upon receiving said entered information, prints an indication on a label wherein the indication that is related to the entered information, and provides instructions to the user to affix the printed label on the eluant reservoir.
5. The radioisotope elution system of any one of items 1 to 4, wherein the information is entered manually by a user on the interface.
6. The radioisotope elution system of any one of items 1 to 5, wherein said information further comprises an expiry date, a batch number, an eluant reservoir, the name of a user who performed said installation, the date of said installation, and/or the time of said installation.
7. The radioisotope elution system of any one of items 1 to 6, wherein the instructions are displayed on the user interface when an eluant reservoir is installed on the system.
8. The radioisotope elution system of any one of items 1 to 7, wherein the system further comprises a camera device, and wherein the user enters said information by using the camera device for taking a picture of the labeling on the eluant reservoir.

9. The radioisotope elution system of item 8, wherein the controller comprises an application that can analyze the picture and identify the type of eluant in the eluant reservoir.
10. The radioisotope elution system of item 8, wherein the controller is configured to provide instructions to a user to use the camera device to take a picture of the label of the eluant reservoir.
11. The radioisotope elution system of item 9, wherein the application is letter recognition application.
12. The radioisotope elution system of item 11, wherein the letter recognition application is able to identify whether the picture comprises the term "NaCl", "saline", "0.9% sodium chloride", "sodium chloride" or any translation thereof.
13. The radioisotope elution system of any one of items 1 to 12, wherein the controller prevents the pump from pumping the eluant into the generator upon the mechanism has identified that the eluant is not a saline solution.
14. The radioisotope elution system of item 1, wherein the liquid parameter detector is adapted to detect the conductivity.
15. The radioisotope elution system of item 1 or 14, wherein the system further comprises a waste container for collecting any eluate that is not infused to a patient, wherein the liquid parameter detector is located in the waste container.
16. The radioisotope elution system of item 1 or 14, wherein the liquid parameter detector is located in the system in an upstream position with respect to the generator.
17. The radioisotope elution system of item 1 or 14, wherein the liquid parameter detector is located in the system in a downstream position with respect to the generator.
18. The radioisotope elution system of any one of items 1 and 14-17, wherein the liquid parameter detector is used on a sample of eluant after an eluant reservoir is installed or replaced.
19. The radioisotope elution system of any one of items 1 and 14-18, wherein the controller prevents the pump from pumping the eluant into the generator upon the liquid parameter detector has detected that said at least one of the parameters is above a predetermined threshold.
20. A radioisotope elution system comprising a radioactive generator containing a parent radioisotope that decays into a corresponding daughter radioisotope, a pump for pumping an eluant into the generator and generating an eluate containing the daughter radioisotope, a patient line for infusing a patient with the daughter radioisotope eluate, a dose calibrator for detecting the parent radioisotope content in a sample of eluate and a controller for controlling the pump, wherein:
   the parent radioisotope contains strontium-85 and/or strontium-82;
   the daughter radioisotope contains rubidium-82;
   the controller is configured for automatically performing a daily quality control test at a pre-determined time of the day that was configured by a user, and
   the daily quality control test comprises the detection of a parent radioisotope content in said sample of the radioisotope eluate.
21. The radioisotope elution system of item 20, wherein said pre-determined time of the day is outside the user working hours.
22. A radioisotope elution system comprising a radioisotope generator containing a parent radioisotope that decays into a daughter radioisotope, a patient line for infusing a patient with a daughter radioisotope eluate generated by the generator, a pump for pumping an eluant from an eluant reservoir into the generator, a controller for controlling the pump, and a scanner for scanning a coded information that is related to at least one of the generator or the patient.
23. The radioisotope elution system of item 22, wherein the coded information is related to the generator, and the controller is configured to use the coded information to determine the available amount of daughter radioisotope.
24. The radioisotope elution system of item 22, wherein the coded information is related to the patient, and the controller is configured to use the coded information to determine at least one of the dose of daughter radioisotope to be infused to the patient, the infusion flow rate, the infusion duration, and any previously received infusion.
25. The radioisotope elution system of any one of items 22 to 24, wherein the coded information is provided by a bar code, a radiofrequency identification code, quick response code, or a magnetic tag.
26. The radioisotope elution system of item 22 or 23, wherein the coded information is related to the generator and contains information about the manufacturing date of the generator, the amount of parent radioisotope that was loaded in the generator at the manufacturing date, the type of parent radioisotope that was loaded, and the generator expiry date.
27. The radioisotope elution system of item 22 or 24, wherein the coded information is attached to the patient and contains at least one of the following patient characteristic: identification, age, sex, body weight, body mass index, body circumference, a surface area intended for imaging, a previous received radioisotope dose, and the time where a previous radioisotope dose was received.
28. A radioisotope elution system comprising a radioisotope generator containing a parent radioisotope that decays into a daughter radioisotope, a patient line for infusing a patient with a daughter radioisotope eluate generated by the generator, a pump for pumping an eluant from an eluant reservoir into the generator, a controller for controlling the system, wherein the system further comprises an audible or visual alert that is displayed when the system is stopped.
29. The radioisotope elution system of item 28, wherein system is stopped after a patient elution, after a quality control test, or when the controller stops the pump upon detecting an error in the system.
30. The radioisotope elution system of item 28 or 29, wherein the visual alert includes a variety of lights or graphics where each light or graphic has a specific color and/or flashing pattern.
31. The radioisotope elution system of item 28 or 29, wherein the audible alert includes a variety of sounds where each sound has a specific frequency, intensity and/or pattern.
32. A radioisotope elution system comprising a radioisotope generator containing a parent radioisotope that decays into a daughter radioisotope, a patient line for infusing a patient with a daughter radioisotope eluate generated by the generator, a pump for pumping an eluant from an eluant reservoir into the generator, a controller for controlling the pump, a dose calibrator adapted for detecting the parent radioisotope in a sample of eluate that was collected in a vial, and a waste container for collecting any eluate that is not infused into the patient, wherein the system further comprises a lifting mechanism for lifting and/or lowering at least one of the vial in the dose calibrator, the generator and the waste container.

33. The radioisotope elution system of item 32, wherein a lifting mechanism is for lifting and/or lowering the vial in the dose calibrator.

34. The radioisotope elution system of item 33, wherein the controller controls the lifting mechanism and prevents the vial from being lifted during a complete duration of a quality control test performed on said sample of eluate.

35. The radioisotope elution system of item 32, wherein the lifting mechanism is for lifting and/or lowering the generator or the waste container.

36. The radioisotope elution system of any one of items 32 to 35, wherein the lifting mechanism is automatic.

37. The radioisotope elution system of any one of items 32 to 35, wherein the lifting mechanism is manual.

38. A radioisotope elution system comprising a radioisotope generator, a patient line for infusing a patient with a radioisotope eluate generated by the generator, a user interface, and a cabinet structure enclosing the generator; wherein the generator can be accessed by a door defined in the cabinet structure, and wherein at least one of the door and the user interface has a user authentication system.

39. The radioisotope elution system of item 38, wherein the user authentication system is a biometric enabled lock, a lock using a bar code identification system, a radiofrequency identification system, a quick response code system, a voice recognition locking/unlocking system, a mechanical lock mechanism.

40. The radioisotope elution system of item 38, wherein the radioisotope elution system further comprises a voice recognition system for receiving input by voice command.

41. The radioisotope elution system of any one of items 38 to 40, wherein the controller in electronic communication with a remote entity that is a remote user device or a remote computer.

42. The radioisotope elution system of item 41, wherein the remote user device or remote computer enables a user to provide a command to the controller; or enables the user to enter a data into the system; and enables the user to receive an information from the elution system.

43. The radioisotope elution system of item 41 or 42, wherein the is a remote user device or remote computer is able to store information from the elution system.

BRIEF SUMMARY OF DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
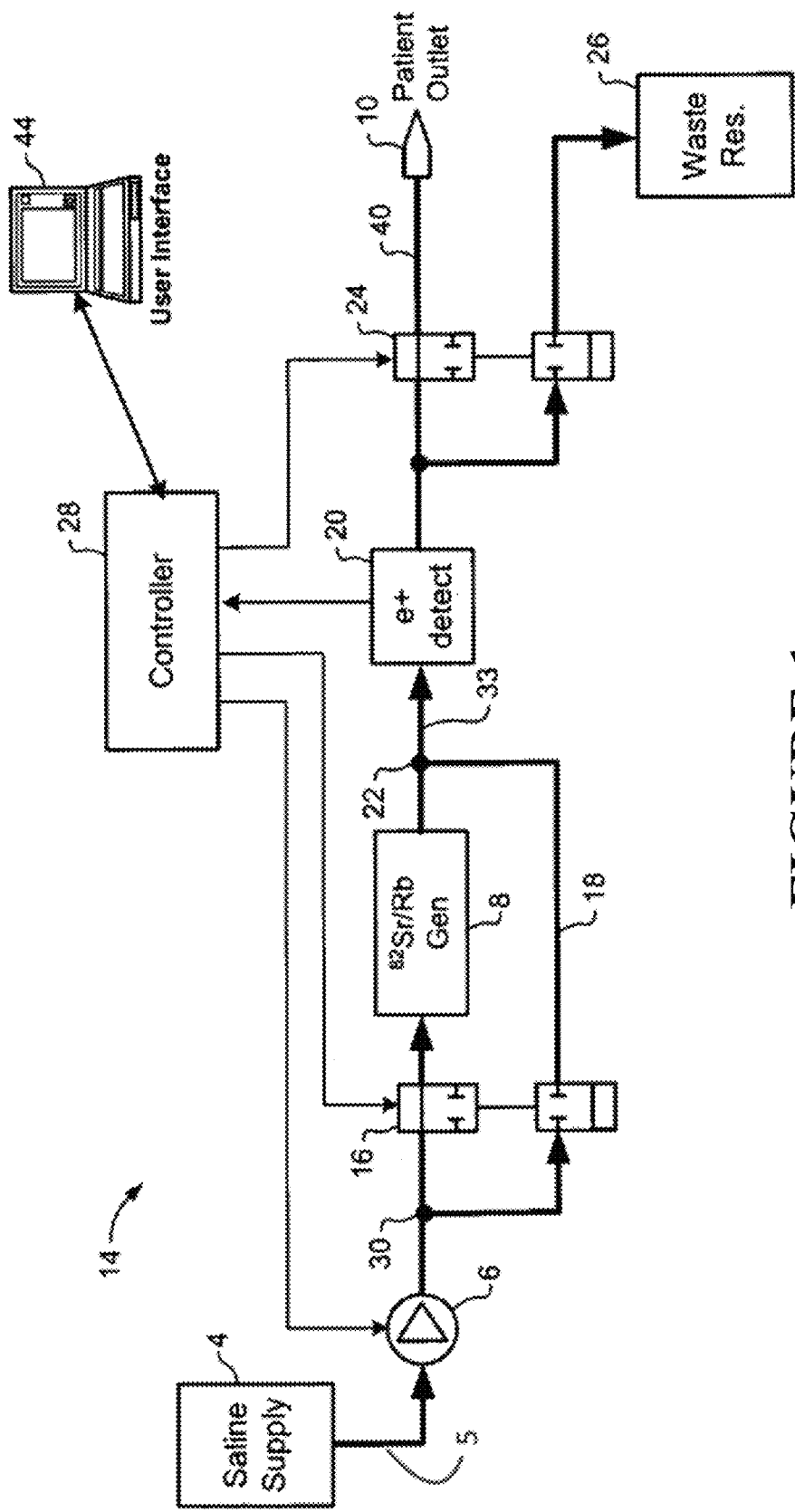
FIG. 1 is a block diagram schematically illustrating principal elements of a rubidium-82 elution system in accordance with an embodiment of the present invention.

The present invention can be more readily understood by reading the following detailed description of the invention and included embodiments.

As used herein, the term "column" refers to the functional component of a radiopharmaceutical generator, wherein a hollow column is packed or loaded with an ion exchange resin, wherein the ion exchange resin is charged with a parent radioisotope. The ion exchange resin has higher affinity for parent radioisotope as compared to daughter radioisotope. Thus, when eluting a suitable medium, the daughter radioisotope is eluted from the generator while the parent radioisotope stays adsorbed to matrix of ion exchange resin. The daughter radioisotope is formed in-situ by radioactive decay of parent radioisotope in the column.

As used herein, the term "generator system" or "generator" or "radioisotope generator" refers to a column containing the parent radioisotope, in a shielded container made of a radiation shielding material that surrounds the columns in order to absorb the energy radiating from the column, and thus protecting the end user from getting exposed to harmful radiation. The radioisotopes which can be used with radioisotope generator include, but are not limited to $^{99}$Mo/$^{99m}$Tc, $^{90}$Sr/$^{90}$Y, $^{82}$Sr/$^{82}$Rb, $^{188}$W/$^{188}$Re, $^{68}$Ge/$^{68}$Ga $^{42}$Ar/$^{42}$K, $^{44}$Ti/$^{44}$Sc, $^{52}$Fe/$^{52}$Mn, $^{72}$Se/$^{72}$As, $^{83}$Rb/$^{83m}$Kr; $^{103}$Pd/$^{103m}$Rh, $^{109}$Cd/$^{109m}$Ag, $^{113}$Sn/$^{113m}$In, $^{118}$Te/$^{118}$Sb, $^{132}$Te/$^{132}$I, $^{137}$Cs/$^{137m}$Ba, $^{140}$Ba/$^{140}$La, $^{134}$Ce/$^{134}$La, $^{144}$Ce/$^{144}$Pr, $^{140}$Nd/$^{140}$Pr, $^{166}$Dy/$^{166}$Ho, $^{167m}$Er, $^{172}$Hf/$^{172}$Lu, $^{178}$W/$^{178}$Ta, $^{191}$Os/$^{191m}$Ir, $^{194}$Os/$^{194}$Ir, $^{226}$Ra/$^{222}$Rn and $^{225}$Ac/$^{213}$Bi.

As used herein, the term "radioisotope regeneration time" or "regeneration time" or "idle time" or "recharge time" refers to the time required for generator system to establish an equilibrium between rate of production of daughter radioisotope and rate of decay of daughter radioisotope. Once the radioisotope has been eluted out from the column, the generator cannot be used again instantly. The generator needs some time for formation of daughter radioisotope by radioactive decay of parent radioisotope and for establishment of equilibrium between rate of production of daughter radioisotope and rate of decay of daughter radioisotope.

As used herein, the terms "radioisotope medical unit" or "radioisotope medical device" or "radioisotope elution system" can be used interchangeably. In an embodiment, it refers to elution system contained in a cabinet structure. Optionally, the medical unit can be carried by a mobile cart.

As used herein, the term "elution system" refers to infusion system meant for generating a solution containing radioisotopes, measuring the radioactivity in the solution, and infusing the solution into a patient. The elution system allows infusing a patient with a radioisotope solution for the purpose of a treatment or a diagnosis.

As used herein, the term "Sr/Rb elution system" or "$^{82}$Sr/$^{82}$Rb elution system" refers to infusion system meant for generating a solution containing $^{82}$Rb, measuring the radioactivity in the solution, and infusing the solution into a patient in order to perform various studies.

As used herein, the term "shielded components" refers to components that are shielded by a radiopaque material or a radiation resistant material. The "shielded components" may include, for instance, a generator, a dose calibrator, an activity detector and/or a waste container. The terms "waste reservoir" and "waste container" are interchangeably used herein.

As used herein, the term "shielded" refers to the condition of being housed within a compartment that provides a barrier to radioactive radiation generated by the radioisotope, or it refers to the condition of being made of a radiation resistant material that covers any radioactive content. The shielding prevents radiation hazard and exposure of an operator or user to unwanted radiation. Said shielding may be made up of any radiation attenuating material including but not limited to depleted uranium (U), lead (Pb), tin (Sn), antimony (Sb), tungsten (W), bismuth (Bi) or any other suitable element or material and any combination thereof.

As used herein, the term "non-shielded components" refers to saline reservoir or controller.

As used herein, the term "eluant" refers to the liquid or the fluid used for selectively leaching out the daughter radioisotopes from the generator column. Preferably, the term "eluant" also refers to the liquid or the fluid used for not leaching out the parent radioisotopes from the generator column As used herein, the term "eluate" refers to a solution containing the eluant mixed with the daughter radioisotope that exits from the generator column. Alternatively, the term "eluate" also refers to a solution comprising the eluant having gone through the generator and containing the daughter radioisotope, which is mixed an eluant that contains no daughter radioisotope and which has gone through the by-pass line.

In an embodiment, the present invention concerns a radiopharmaceutical elution system comprising a suitable eluant contained in an eluant reservoir, a generator containing a parent radioisotope that decays into a corresponding daughter radioisotope, a first tubing system interconnecting the eluant reservoir and the generator, a pump for pumping the eluant from the eluant reservoir through said first tubing system, a first valve located on said tubing system and downstream the pump for directing the eluant to the generator or to a by-pass line, an eluate exiting the generator through a second tubing system and containing the daughter radioisotope, the second tubing system having a connection to receive the eluant from the by-pass line, a radioactivity detector on the second tubing system downstream said connection, a second valve on the second tubing system downstream the detector for directing the eluate to a patient line or to a waste line that is connected to a waste reservoir, the patient line is adapted for infusing a patient with the eluate, a controller for controlling the pump, the first valve and the second valve, and for receiving the information from the detector.

In an embodiment, the radiopharmaceutical elution system is a rubidium-82 ($^{82}$Rb) elution system, which comprises the components described in FIG. 1. In an embodiment, the elution system comprises reservoir 4 of sterile saline solution (e.g. 0.9% Sodium Chloride Injection); a pump 6 for drawing saline from the reservoir 4 through the supply line 5 and the generator line (between 30 and 22) at a desired flow rate; a generator valve 16 for proportioning the saline flow between a strontium-rubidium ($^{82}$Sr/$^{82}$Rb) generator 8 and a bypass line 18 which circumvents the generator 8; a positron detector 20 located downstream of the merge point 22 at which the generator and bypass flows merge; and a patient valve 24 for controlling supply of active saline to a patient outlet 10 and a waste reservoir 26. A controller 28 is preferably connected to the pump 6, positron detector 20 and valves 16 and 24 to control the elution system 14 in accordance with a desired control algorithm.

Figure 2:
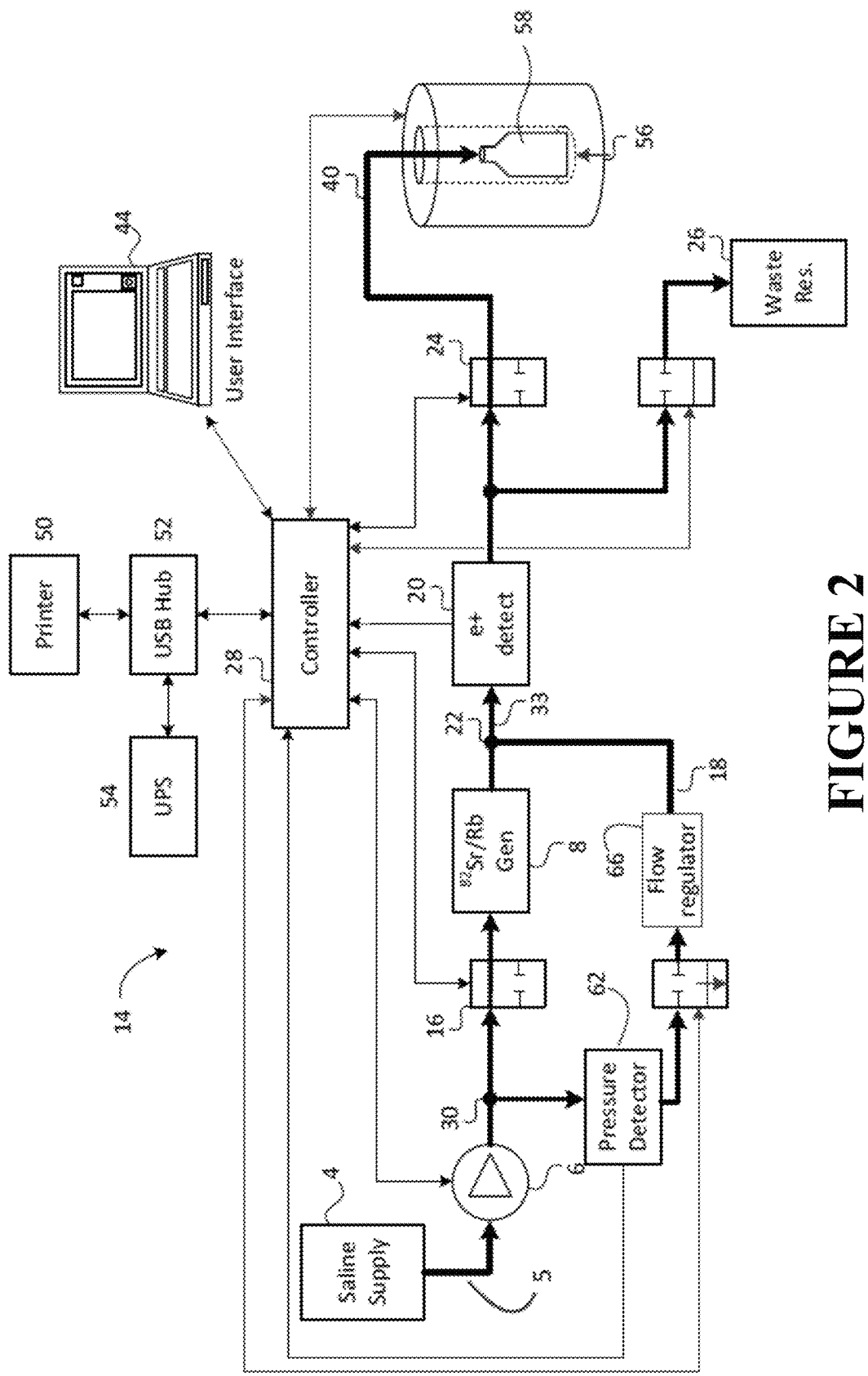
FIG. 2 is a block diagram schematically illustrating principal elements of a rubidium-82 elution system in accordance with another embodiment of the present invention.

FIG. 2 is a block diagram schematically illustrating principal elements of a Rubidium elution system in accordance with another embodiment of the present invention. The Rubidium elution system of FIG. 2 has similar elements as the Rubidium elution system of FIG. 1, and additional elements. These additional elements preferably include one or more of a printer 50 and USB (Universal Serial Bus; or other communications port) port 52, a pressure detector 62, a dose calibrator 56, a flow regulator 66, or a UPS (Uninterruptible Power Supply) 54.

The Rubidium elution system of FIG. 2 may be used to assess various aspects of the system, such as a concentration of $^{82}$Rb, $^{82}$Sr, or $^{85}$Sr in a fluid that is eluted from the generator, the volume of the fluid that is eluted from the generator, or the pressure of the fluid flowing through at least one portion of the system. Information about these aspects of the system may be gathered by various elements of the system, and sent to the controller. The controller and/or user interface (which may comprise a processor and memory) may analyze this gathered data to assess the state of the system.

As shown in FIG. 2, the pressure detector 62 is configured to detect the in-line pressure of the bypass line or the pressure of the generator line, depending on the flow path controlled by the pinch valves, and to convey information about this pressure to the controller. The pressure detector may be configured to detect the in-line pressure elsewhere within the system, such as the feed-line (saline supply-line).

The user interface is depicted as being connected to a printer 50, and having a USB port. The user interface may be used to display an output based on a result of the assessment The printer 50 may be used to print out information about the state of the system, such as a concentration of $^{82}$Rb, $^{82}$Sr, or $^{85}$Sr in a fluid that is eluted from the generator, the volume of the fluid that is eluted from the generator, or the pressure of the fluid flowing through at least one portion of the system. The USB port may be used to store an indication of the result of an assessment in a memory location, such as a flash drive.

In addition, the user interface may be configured to communicate with a remote computer, such as a server, or a cloud computing service. The user interface may communicate all kind of information including the result of an assessment, a detected information, the doses being eluted from the generator or the like, to a controller via a communication network. The remote computer may collect information from multiple computers, and use this collected information to identify the state of a single elution system, or aggregate statistics for multiple $^{82}$Sr/$^{82}$Rb elution systems.

In an embodiment of the invention, the elution system can be operated/controlled from remote device like mobile, tablet or any other like device from distance with the aim of minimizing radiation exposure to the medical personal operating the system. In addition, the user interface may be configured to communicate with a remote computer, such as a server, or a cloud computing service. The user interface may be used to upload an indication of the result of the assessment to a controller via a communication network. The remote computer may collect information from multiple computers, and use this collected information to identify the state of a single elution system, or aggregate statistics for multiple $^{82}$Sr/$^{82}$Rb elution systems.

The elution system of FIG. 2 may additionally have a dose calibrator 56. The dose calibrator 56 may be used instead of a patient outlet, or in addition to a patient outlet, along with a valve 24 that may be configured to direct fluid to the patient outlet or to the dose calibrator. The dose calibrator 56 may comprise a vial 58 (such as a 50 mL vial) that collects the fluid as it otherwise exits the elution system. The dose calibrator 56 may be communicatively coupled to the controller, and configured to send information to the controller, such as an activity concentration of $^{82}Rb$, $^{82}Sr$, or $^{85}Sr$ in a fluid that is eluted from the generator. The dose calibrator 56 may include a radioactivity shielding material.

In certain embodiments, the system is embodied in a portable (or mobile) cart that houses some or all of the generator, the processor, the pump, the memory, the patient line, the bypass line, the positron detector, and/or the dose calibrator.

As used herein, the term "cabinet" refers to the outer structure stretching upward from platform surface of cart wherein the cabinet structure house all or almost all the shielded and non-shielded components of the system. The cabinet structure may be made up of any of the radiation resistant material including but not limited to stainless steel, injection-molded polyurethane or any other suitable materials and combinations thereof fitted together according to methods known to those skilled in the art. In an embodiment, the cabinet can be made of a shielding material.

As used herein, the term "quality control test" refers to the tests performed on daily basis for evaluating the safety and efficacy of elution system and more precisely the generator system. If any of the quality control tests fail, then the generator system is configured to not perform a patient elution. In order to not perform an elution, the controller may stop the pump, set the valves to off, or do a combination of both. Quality control measures may include, but are not limited to, checking and/or testing the status of the generator column, and breakthrough testing, flow rate, leakage, column and tubing pressure, activity of parent and daughter isotopes, sensors and valves functioning, checking the environment surrounding elution system, testing outputs produced by each of the columns, and/or performing testing on samples of the radiopharmaceuticals produced by columns, among other quality control measures. Quality control system may be used to generate one or more quality reports relating to the quality of the radiopharmaceuticals produced by the elution system. Quality reports may include, but are not limited to: analytical tests performed on the product; total yield of the products; failure reports for the product; failure reports for the one or more systems used to manufacture the product; and/or operator error reports, among other quality reports. Quality control system may communicate with each individual system when performing the quality control tests.

In an embodiment, the radiopharmaceutical elution system comprises a suitable eluant contained in an eluant reservoir, a radioactive generator containing a parent radioisotope that decays into a corresponding daughter radioisotope, a first tubing system interconnecting the eluant reservoir and the generator, a pump for pumping the eluant from the eluant reservoir through said first tubing system, a first valve located on said first tubing system and downstream the pump for directing the eluant to the generator or to a by-pass line, an eluate exiting the generator through a second tubing system and containing the daughter radioisotope, the second tubing system having a connection to receive the eluant from the by-pass line, a radioactivity detector on the second tubing system downstream said connection, a second valve on the second tubing system downstream the detector for directing the eluate to a patient line or to a waste line that is connected to a waste reservoir, a patient line is adapted for infusing the eluate to a patient, and a controller for controlling the pump, the first valve and the second valve, and for receiving the information from the detector.

In an embodiment, the radiopharmaceutical elution system comprises at least a radioisotope generator, a patient line for infusing a patient with a radioisotope eluate generated by the generator, an eluant reservoir, a pump for pumping eluant from the eluant reservoir to the generator, and a controller for controlling the pump.

In an embodiment, the radiopharmaceutical elution system comprises a suitable eluant contained in an eluant reservoir, a radioactive generator containing a parent radioisotope that decays into a corresponding daughter radioisotope, a first tubing system interconnecting the eluant reservoir and the generator, a pump for pumping the eluant from the eluant reservoir through said first tubing system, a first valve located on said first tubing system and downstream the pump for directing the eluant to the generator or to a by-pass line, an eluate exiting the generator through a second tubing system and containing the daughter radioisotope, the second tubing system having a connection to receive the eluant from the by-pass line, a radioactivity detector on the second tubing system downstream said connection, a second valve on the second tubing system downstream the detector for directing the eluate to a patient line or to a waste line that is connected to a waste reservoir, the patient line is adapted for infusing the eluate to a patient, a controller for controlling the pump, the first valve and the second valve, and for receiving the information from the detector, wherein the controller is connected to an imaging software of a radioisotope imaging device that is arranged for imaging the patient receiving the radioisotope infusion or a region of said patient.

In an embodiment, the radiopharmaceutical elution system of the present invention further comprises a user interface that allows the user to enter various commands and data of the patient, the eluant reservoir and/or the generator, or the type of desired patient elution (dose, speed, duration). The terms "patient elution" and "patient infusion" are used interchangeably herein and refers to an eluate exiting the generator and containing the daughter radioisotope that is administered to a patient through intravenous or intra-arterial administration.

The radiopharmaceutical elution systems are complex and there exists high risk of radiation hazard and accidental exposure to user. Unauthorized access to components of generator system and elution system can be hazardous and may cause radiation related health hazards not only to the user but also to the persons present around vicinity. Therefore, to overcome this problem, one embodiment of the present invention relates to a cabinet structure of radioisotope elution system having a door with a user authentication system, for preventing unauthorized access to the generator and elution system components.

In an embodiment, the system of the present invention has user interface which comprises a user authentication system. The door user authentication system and the interface user authentication system can be independently embodied by a biometric enabled lock, a lock using a bar code identification system, a radiofrequency identification (RFID) system, a quick response (QR) code system, a voice recognition locking/unlocking system, a mechanical lock mechanism, or any other locking mechanism.

The interface user's authentication system can be similar to the door locking mechanism and can be, without limitation, a biometric enabled lock, a lock having a scanner for identifying a bar code label or a radiofrequency identification (RFID) tag, a voice recognition locking/unlocking system, or a mechanical lock mechanism, or any other locking mechanism.

In an embodiment, the elution system has a voice recognition system that enables a user to input a command. In another embodiment, the user interface is a touch screen. In yet another aspect, the user interface is comprised in a screen mounted on a foldable support, a retractable support or any combination thereof. In a further embodiment, the radiopharmaceutical elution system of the present invention further comprises a speaker and/or a light display mechanism and/or an interface. Advantageously, the speaker provides sounds of various frequency, intensity and/or patterns and the light display mechanism may feature lights or graphics of various colors or flashing patterns which in combination or not, provide a distinctive audible and/or visual alert for a specific condition of the system. In another embodiment, said graphics are displayed on the interface. In an embodiment, an audible and/or visual alert that is displayed when the system is stopped. The situations where the system is stopped include, without limitation, after a patient elution, after a quality control test, or when the controller stops the pump upon detecting an error in the system. In these situations, the audible and/or visual alert allows the user to be aware that the system has stopped and to undertake immediately the next action if desired. The next action can be a further patient elution, or fixing the error that was detected. Examples of errors include, without limitation, maximum allowed time for activity threshold is exceeded, only 4 patient infusions are allowed before additional breakthrough checks, system detected a pinch valve problem, daily constancy check is needed, daily check standard is not configured, daily quality control is required, communication error with the calibrator, dose calibrator isotope is not configured correctly, dose calibrator is not responsive, daily generator flush is needed, the generator eluted volume reached the allowed limit, high pressure detected in the tubing, software failed to initialize some equipment, the activity received during calibration is not valid (too low), the activity ratio between dose calibrator and radioactivity counter is not valid, generator setting are invalids, UPS battery level is low, low pressure detected in the tubing, system cannot generate flow within specifications, dose calibrator activity decay is not linear, power failure detected, maximum volume reached for this patient, system detected failure with the pressure transducer, system detected a failure with the pump, pump speed is higher than expected, pump speed is lower than expected, communication failure with the radioactivity counter, system detected a failure with the radioactivity counter, the radioactivity counter is exposed to light, available saline volume is not sufficient for this operation, daily setup verification is needed, the breakthrough limit level is reached and patient infusion is not allowed, the breakthrough warning level is reached and a limit of 4 patient infusions is allowed before a new quality control is performed, UPS power disconnection detected, communication between the controller and UPS has been lost, waste reservoir needs to be emptied, system is in maintenance mode, and incorrect personal identification number (PIN) has been entered.

In another embodiment of the present system, the system has a "software switch" or simply a menu in settings which needs to be turned off, before removal of the critical components of the system from their place for routine changing, cleaning or any other purpose. The said menu is protected by an authentication mechanism which can be same as that of user authentication mechanisms for unlocking the system or different than that with enhanced administrator privileges. If a user or an unauthorized user tries to tamper with the critical components of the system without authenticating, then the controller will at least lock the complete system centrally, disconnect the power supply to the components and/or notify the maintenance and law enforcement agencies silently that someone is trying to tamper with the system. Optionally, a hardware based panic button can also be incorporated on the system for voluntary locking of the system and notifying the local enforcement agency in case of an emergency situation. The panic button or the software switch will cease the complete elution system and its operation for at least 30 minutes. The system cannot be reused before completion of this time period. After the completion of this time period, the system preferably needs to be recalibrated before the system can be reused. Further, to enhance the security, a combination of more than one authenticating mechanisms present with different sources is required for unlocking the system before use. The combination of more than one authenticating mechanisms is particularly recommended after the panic button or the activation of software switch have been used. The said different sources for authenticating may include different passwords/biometric authentication/voice recognition or any related mechanism available with different users/operators/individuals/authorities.

In another embodiment, similar mechanism can be used for keeping the data related to patients secure, to prevent any breach of data as per regulatory requirements.

In an embodiment of the invention, the controller is accessible remotely for servicing, giving commands, system alerts, image exports, image acquisition, start or stop of infusion, quality control tests and analysis of performance data. According to this embodiment, the controller is in electronic communication with a remote computer that is enabled to store information from the elution system such as data entered by a user, image acquisition data, a quality control test result, a performance data of the system, and/or detected error.

In an embodiment, the system of the present invention is automated so as to start and perform daily a quality control test at a pre-determined time. The user may take advantage of setting said pre-determined time outside his/her working hours in order to not waste any time with proceeding to said quality control test and using all of his/her time for performing patient elutions.

According to a preferred embodiment, the daughter radioisotope generated by the generator is rubidium-82. The quality control test (also called breakthrough) is the measurement of any residual amount of the parent radioisotope (strontium-82) and contaminant radioisotope (strontium-85) that leak out the generator column. In an aspect of the invention, the acceptable limits for the quality control test result are in accordance with limits defined in USP. In another aspect of the invention, the acceptable limits for the quality control test result are 0.01 µCi of $^{82}Sr/mCi$ of $^{82}Rb$ and 0.1 µCi of $^{85}Sr/mCi$ of $^{82}Rb$.

In another aspect of the invention, the controller blocks the system from performing a patient infusion until a quality control test is performed with results that are within the acceptable limits. In order to obtain result within acceptable limits, a second quality control test can be performed. If the acceptable limits are not reached, replacement of the generator is needed. In this case, the controller is configured to prevent the system from performing a patient infusion and allows the system to only perform i) a quality control test, ii) a calibration test for calibrating the dose calibrator and iii) a flush elution for flushing the tubing line circuit with the eluant so as to remove any air bubble.

In another embodiment, the radiopharmaceutical elution system of the present invention further comprises a scanner for scanning a coded information related to the generator and/or the patient. When the coded information is related to the generator, and the controller is configured to use the coded information to determine the available amount of daughter radioisotope. When the coded information is related to the patient, and the controller is configured to use the coded information to determine at least one of the dose of daughter radioisotope to be infused to the patient, the infusion flow rate, the infusion duration, and any previously received infusion. This advantageously prevents user from entering error. The scanner can be adapted for scanning, without limitation, a bar code, an RFID (Radio Frequency Identification) code, a QR (Quick Response) code, a magnetic code or any other similar technology. Advantageously, the scanner can be used for keying the information present on a generator about the radioactivity contained in it at the time of manufacturing and calculate the radioactivity that remains therein after a known decay period. This information may contain, without limitation, the manufacturing date of the generator, the amount of parent radioisotope that was loaded in the generator at the manufacturing date, the type of parent radioisotope that was loaded in the generator at the manufacturing date, and the generator expiry date. The coded information can be attached directly on the generator or on its packaging slip.

The information to be scanned from a patient can be stocked in a bracelet, a card, with the patient file, or any other means. Such information may contain the patient identification, information about any previous radioactive elution that the patient has already received, the patient characteristics for supporting the determination of the adequate radioactive dose that the patient shall receive to obtain the best imaging quality, such as, without limitation, age, body weight, body mass index, body circumference or a surface area of a region intended for imaging.

In another embodiment, the radioisotope elution system comprises a lifting mechanism for lifting and/or lowering a vial in the dose calibrator. Advantageously, the controller may control the lifting mechanism. In an embodiment, the controller prevents the vial from being lifted out the dose calibrator during the quality control test. This embodiment may serve to keep the vial in place (inside the dose calibrator) and prevent a user from tampering and/or interfering with the vial while a quality control test is performed.

Advantageously, the lifting mechanism of the vial in the dose calibrator locks the vial in the dose calibrator during the whole duration of the quality control test which starts when the sample is poured in the vial and until the strontium content is detected.

In a further embodiment of the present invention, the radioisotope elution system comprises a lifting mechanism that is controlled by the controller, for lifting and/or lowering the generator. The lifting mechanism can be automatic. Alternatively, the lifting mechanism can be manual such a crank or a lever engaged by a user. The generator needs to be well shielded and thus it is relatively heavy. Advantageously, the lifting mechanism of the generator renders manipulation of the generator and its replacement safer for the user.

In another embodiment, the radioisotope elution system comprises an automatic lifting mechanism for lifting and/or lowering the waste reservoir. Advantageously, the lifting mechanism of the waste reservoir can be controlled remotely and thus allowing safer removal of the waste reservoir that still contains radioactivity that has not yet decayed. It is envisioned that any lifting mechanism discussed herein can also be remotely controlled.

In an embodiment of the present invention, the system further comprises a sensor that is incorporated therein, for real time monitoring of pH of any solution, including the eluant or the eluate or both.

In an embodiment of the present invention, the controller is communicatively coupled to the dose calibrator via a wired or a wireless connection.

In an embodiment of the present invention, the system has provision for automatic emptying of the waste container when the volume of waste liquid therein reaches a specified volume, or reaches up to a specified mark, or at specific intervals of time.

In an embodiment of the present invention, the waste reservoir has a disposable waste bag therein in order to ease disposal of the waste liquid.

In an embodiment of the invention, the elution system further comprises means for carrying medical supplies or elution system supplies, including but not limited to, tubing, disposable waste bags, vials, bottle, bucket, vessel, drum, canister, pig-shield, bin, gloves, a stress agent source, and/or a resuscitation aid device.

According to another embodiment of the invention, the controller of the radioisotope elution system is configured to provide instructions to the user to enter the number written under the bar code of the eluant reservoir (which is preferably a saline bag), and/or the NDC (National Drug Code) number which is included in the number underneath the bar code, and/or the expiry date of the eluant reservoir, and/or the batch number, and/or the DIN (Drug Identification Number), and/or the name of the user who has installed the eluant reservoir, and/or the date and time of installation of said eluant reservoir. Preferably, the user enters this information manually on the user interface. In this embodiment, the bar code is not used, and a bar code scan reader is not used. The controller provides these instructions to the user interface when an eluant reservoir is installed or replaced. These instructions are preferably shown on the user interface. In a preferred embodiment, the system further comprises a printer which prints information on a tag that is in relation with the information entered by the user. Preferably, the controller further provides instructions to the user to affix the printed tag on the eluant reservoir. In the case that the user has entered information that allows the controller to determine that the eluant reservoir contains a liquid that is not an appropriate saline solution, the controller prevents the pump from pumping the detected inappropriate eluant into the generator, and further instructions are provided to the user so as to replace the eluant reservoir with an appropriate eluant reservoir.

According to another embodiment of the invention, the radioisotope elution system further comprises a camera device for taking a picture of a label on the eluant reservoir, and the controller has an application that analyses the picture and identifies the type of eluant in the eluant reservoir. In an embodiment, the application is a letter recognition application that identifies whether the pictured name consists of the expression "0.9% sodium chloride", "sodium chloride" "saline", "NaCl" or any translation thereof. In another embodiment, the controller provides instructions to the user when installing an eluant reservoir to take a picture of a label on said new eluant reservoir. These instructions are preferably shown on the user interface. In the case that the identified type of eluant is not a saline solution, the controller prevents the pump from pumping the inappropriate eluant into the generator, and further instructions are provided to the user so as to replace the eluant reservoir with an appropriate eluant reservoir.

According to another embodiment of the invention, the radioisotope elution system further comprises a detector or a sensor for measuring a liquid parameter such as:
- the pH: Saline solution has a pH of about 5.5 whereas lactated ringer solution has a pH of about 6.5. The preferred predetermined threshold is 5.7, 5.8, 5.9, or 6.0.
- the refractive index: In optics, the refractive index or index of refraction of a material is a dimensionless number that describes how fast light propagates through the material. This value is determined by the speed of light in vacuum and by the phase velocity of light in the medium. For example, the refractive index of water is 1.333, meaning that light travels 1.333 times faster in vacuum than in water.
- the presence or quantity of divalent ions or trivalent ions: Saline solution contains sodium and chloride; whereas lactated ringer solution contains sodium, chloride, potassium, calcium, and lactate in the form of sodium lactate. The predetermined threshold is preferably the absence of divalent ions or trivalent ions, or lower than is less than 100 ppm.
- the conductivity of the eluant is preferably in the range of 12-20 ms/cm.
- the Piezoelectricity: Determination of divalent cations, such as Ca(2+) and Mg(2+), in a liquid medium can be achieved using an ion chromatography method, in which a piezoelectric quartz crystal (PQC) sensor was used as a detector (Yu et al. 2002 J. Pharm. Biomed. Anal., 29(5):969).
- the atomic absorption spectroscopy: Atomic absorption spectroscopy is based on absorption of light by free metallic ions.
- the photoelectric flame photometry: Photoelectric flame photometry is a branch of atomic spectroscopy that uses for inorganic chemical analysis for determining the concentration of certain metal ions such as sodium, potassium, lithium, calcium, Cesium, etc.
- the atomic emission spectroscopy (AES): Atomic emission spectroscopy (AES) is a method of chemical analysis that uses the intensity of light emitted from a flame, plasma, arc, or spark at a particular wavelength to determine the quantity of an element in a sample. This method is useful for determining trace metals in liquids and is almost independent of the molecular form of metal in the sample. These methods are very sensitive and can detect different metals in concentrations as low as 1 ppm.
- the inductively coupled plasma atomic emission spectroscopy (ICP-AES) also referred to as inductively coupled plasma optical emission spectrometry (ICP-OES): This is an analytical technique that is used for the detection of chemical elements. It is a type of emission spectroscopy that uses the inductively coupled plasma to produce excited atoms and ions that emit electromagnetic radiation at wavelengths characteristic of a particular element.
- the inductively coupled plasma mass spectrometry (ICP-MS): ICP-MS is a type of mass spectrometry which is capable of detecting metals and several non-metals at concentrations as low as one part in 1015 (part per quadrillion, ppq) on non-interfered low-background isotopes. This is achieved by ionizing the sample with inductively coupled plasma and then using a mass spectrometer to separate and quantify those ions.
- the ability to form a complex with a complexing agent such as EDTA—(a test sample can be collected during the quality control or at another time and tested for its ability to complex a complexing agent by titration).
- the fluorescence as detected by X-ray fluorescence (XRF) or other means.
- the element content as detected by a particle-Induced X-Ray Emission (PUCE).

In another aspect, the divalent ions are selected from group consisting of Barium($2^+$), Beryllium($2^+$), Cadmium($2^+$), Calcium($2^+$), Chromium($2^+$), Cobalt($2^+$), Copper($2^+$), Europium($2^+$), Gadolinium($2^+$), Germanium($2^+$), Iron($2^+$), Lanthanum($2^+$), Lead($2^+$), Magnesium($2^+$), Manganese($2^+$), Mercury($2^+$), Nickel($2^+$), Osmium($2^+$), Platinum($2^+$), Ruthenium($2^+$), Strontium($2^+$), Tin($2^+$), Uranium($2^+$), Vanadium($2^+$), Yttrium($2^+$), and Zinc($2^+$). In another aspect, the trivalent ions are selected from group consisting Iron($3^+$), Cadimium($3^+$), Aluminum($3^+$) and Boron($3^+$).

For sake of simplicity, the detector or sensor for measuring a liquid parameter is called herein a "liquid parameter detector". The liquid parameter detector, is preferably adapted to detect in the eluant or the eluate at least one of the following parameters:
a. pH,
b. refractive index,
c. presence divalent ions or trivalent ions,
d. quantity of divalent ions or trivalent ions,
e. conductivity,
f. piezoelectricity,
g. light absorbance (detected by atomic absorption spectroscopy, based on absorption of light of free metallic ions),
h. photoelectricity (detected by flame photometry), atomic emission (detected by atomic emission spectroscopy (AES)),
i. optical emission (detected by inductively coupled plasma atomic emission spectroscopy (ICP-AES) also referred to as inductively coupled plasma optical emission spectrometry (ICP-OES)),
j. atomic mass (detected by inductively coupled plasma mass spectrometry (ICP-MS)),
k. EDTA complexing ability,
l. Fluorescence (detected by X-ray fluorescence (XRF))
m. Element content (particle-Induced X-Ray Emission (PIXE)).

Said liquid parameter detector can be located in the waste reservoir, upstream the generator or downstream the generator. In the waste reservoir includes in the cover of the waste reservoir or inside the reservoir where the eluate is collected. Upstream the generator includes the first tubing system interconnecting the eluant reservoir and the generator. Downstream the generator includes the by-pass line and the second tubing system, the patient line, the waste line and the waste reservoir. The liquid parameter detector can be used on a sample of eluant after an eluant reservoir is installed or replaced. Preferably, the controller prevents the pump from pumping the eluant into the generator upon liquid parameter detector has detected that said at least one of the parameters is above a predetermined threshold.

In a further embodiment of the invention, the controller of the radioisotope elution system further provides instructions to use an eluant reservoir that is recommended by the manufacturer of the radioisotope elution system. In an embodiment, wherein said recommended eluant reservoir is sold by the manufacturer and contains a saline solution. In an embodiment, incorrect eluant includes, without limitation, dextrose solution, saline solution having a concentration different than 0.9%, and lactated ringer.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope, and spirit of this invention. A system comprising any combination of the described features and embodiments is encompassed by the present invention. All permutation and combination are not listed for sake of conciseness.

What is claimed:

1. A radioisotope elution system comprising a radioisotope generator containing a parent radioisotope that decays into a daughter radioisotope, a patient line for infusing a patient with a daughter radioisotope eluate generated by the generator, a pump for pumping an eluant from an eluant reservoir into the generator, a controller, and a user interface, wherein the system has at least mechanism for identifying whether the eluant is a saline solution or not, said mechanism comprises
　　a liquid parameter detector, wherein the liquid parameter detector that is adapted to detect in the eluant at least one of the following parameters:
　　i. pH,
　　ii. quantity of divalent ions or trivalent ions,
　　iii. piezoelectricity,
　　iv. light absorbance detected by atomic absorption spectroscopy, based on absorption of light of free metallic ions,
　　v. photoelectricity detected by flame photometry, atomic emission detected by atomic emission spectroscopy (AES),
　　vi. optical emission detected by inductively coupled plasma atomic emission spectroscopy (ICP-AES) also referred to as inductively coupled plasma optical emission spectrometry (ICP-OES),
　　vii. atomic mass detected by inductively coupled plasma mass spectrometry (ICP-MS),
　　viii. EDTA complexing ability,
　　ix. fluorescence detected by X-ray fluorescence (XRF)
　　x. element content detected by a particle-Induced X-Ray Emission (PIXE).

2. The radioisotope elution system of claim 1, wherein the system further comprises a printer, and wherein the controller controls the printer and, upon receiving said entered information, prints an indication on a label wherein the indication that is related to the entered information, and provides instructions to the user to affix the printed label on the eluant reservoir.

3. The radioisotope elution system of claim 1, wherein the information is entered manually by a user on the interface.

4. The radioisotope elution system of claim 1, wherein the instructions are displayed on the user interface when an eluant reservoir is installed on the system.

5. The radioisotope elution system of claim 1, wherein the system further comprises a camera device, and wherein the user enters said information by using the camera device for taking a picture of the labeling on the eluant reservoir.

6. The radioisotope elution system of claim 5, wherein the controller comprises an application that can analyze the picture and identify the type of eluant in the eluant reservoir.

7. The radioisotope elution system of claim 5, wherein the controller is configured to provide instructions to a user to use the camera device to take a picture of the label of the eluant reservoir.

8. The radioisotope elution system of claim 6, wherein the application is letter recognition application.

9. The radioisotope elution system of claim 8, wherein the letter recognition application is able to identify whether the picture comprises the term "NaCl", "saline", "0.9% sodium chloride" "sodium chloride", or any translation thereof.

10. The radioisotope elution system of claim 1, wherein the controller prevents the pump from pumping the eluant into the generator upon the mechanism has identified that the eluant is not a saline solution.

11. The radioisotope elution system of claim 1, wherein the system further comprises a waste container for collecting any eluate that is not infused to a patient, wherein the liquid parameter detector is located in the waste container.

12. The radioisotope elution system of claim 1, wherein the liquid parameter detector is located in the system in an upstream position with respect to the generator.

13. The radioisotope elution system of claim 1, wherein the liquid parameter detector is used on a sample of eluant after an eluant reservoir is installed or replaced.

14. The radioisotope elution system of claim 1, wherein the controller prevents the pump from pumping the eluant into the generator upon the liquid parameter detector has detected that said at least one of the parameters is above a predetermined threshold.

* * * * *